(12) United States Patent
Ryan (10) Patent No.: US 7,066,936 B2
(45) Date of Patent: Jun. 27, 2006

(54) SURGICAL CUTTING AND TISSUE VAPORIZING INSTRUMENT

(75) Inventor: Thomas P. Ryan, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 136 days.

(21) Appl. No.: 10/862,208

(22) Filed: Jun. 7, 2004

(65) Prior Publication Data

US 2005/0273097 A1 Dec. 8, 2005

(51) Int. Cl.
*A61B 18/18* (2006.01)
(52) U.S. Cl. .............................. 606/45; 606/41; 606/48
(58) Field of Classification Search .................. 606/45
See application file for complete search history.

(56) References Cited

U.S. PATENT DOCUMENTS

| 5,348,554 | A | * | 9/1994 | Imran et al. | ................... | 606/41 |
| 5,458,597 | A | * | 10/1995 | Edwards et al. | ............... | 606/41 |
| 2003/0125732 | A1 | * | 7/2003 | Goble | ........................ | 606/48 |
| 2003/0130658 | A1 | * | 7/2003 | Goble et al. | ................... | 606/48 |

* cited by examiner

*Primary Examiner*—Michael Peffley
*Assistant Examiner*—Alex Toy (57) ABSTRACT

A surgical cutting and tissue vaporizing instrument, also referred to as an electrosurgical instrument, is in the form of a scalpel or scissors. The scalpel has a handle portion and a blade portion mounted on the handle portion. The blade portion has a smaller front section which acts as an active electrode, a larger rear section which acts as a return electrode, and an insulating middle section separating the two electrodes. A plurality of ports and conduits are formed in the blade portion, with the conduits extending through the handle portion, so that saline may be supplied to the handle and blade portions and out of the ports to the targeted area for tissue transection, and so that excess saline may be drawn by suction through other ports formed on the blade portion. The scissors include two cross-pivotally joined blades, each having a tip portion functioning as either an active electrode or as a return electrode. Ports and conduits are formed in each blade to elute saline onto the targeted area for tissue transection and to remove by suction excess saline from the targeted area.

12 Claims, 8 Drawing Sheets

FIG. 8 ns and intrauterine septa. An example of an
SURGICAL CUTTING AND TISSUE VAPORIZING INSTRUMENT

BACKGROUND OF THE INVENTION

1. Field of the Invention

This invention relates to surgical cutting instruments, and more particularly relates to electrosurgical scalpels and scissors.

2. Description of the Prior Art

Electrosurgical vaporization is a medically accepted procedure very often used to remove submucous fibroids, polyps, adhesions and intrauterine septa. An example of an electrosurgical vaporization device is the VersaPoint™ bipolar electrosurgery system marketed by Gynecare Worldwide, a division of Ethicon, Inc. With such a device, a localized RF (radio frequency) current flows through a physiological compatible fluid medium, such as saline, at the surgical site, in this case, the patient's uterus, whereupon an electrode tip of the instrument is energized and contacts the endometrium (i.e., the lining of the uterus) to vaporize the targeted tissue. The advantage of this procedure, and vaporization procedures in general, is that it facilitates tissue removal or cutting while simultaneously providing hemostasis.

Electrosurgical transecting instruments employing RF energy are also well known and commonly used in arthroscopic surgery. For example, the various ArthroWand™ surgical devices marketed by ArthroCare Corporation uses RF bipolar energy provided to spaced apart electrodes in a conductive medium, such as saline, to excite the electrolytes therein and thereby create a focused, energized plasma between the electrodes to cut or dissolve the targeted tissue while simultaneously sealing any bleeding vessels (i.e., effecting hemostasis).

There are also currently used electrosurgical blades and scissors. Ordinary, non-energized scalpels or scissors used in surgery result in tissue bleeding. Electrosurgical scalpels, and monopolar or bipolar scissors, transect tissue and simultaneously provide tissue cauterization to minimize bleeding. However, such electrosurgical instruments are used in a dry environment. Invariably, the surgical procedure in which they are used must be periodically interrupted so that the cutting surfaces of these instruments may be cleaned, thus prolonging the surgical procedure.

OBJECTS AND SUMMARY OF THE INVENTION

It is an object of the present invention to provide an electrosurgical instrument that can transect tissue with hemostasis.

It is another object of the present invention to provide an electrosurgical cutting and tissue vaporizing instrument that uses localized RF (radio frequency) current flow.

It is yet another object of the present invention to provide an electrosurgical cutting and tissue vaporizing instrument that has electrodes and uses saline wetting between the electrodes to localize current flow through the targeted tissue.

It is yet a further object of the present invention to provide an electrosurgical cutting and tissue vaporizing instrument that is self-wetting.

It is still a further object of the present invention to provide a self-wetting electrosurgical cutting and tissue vaporizing instrument that may be used in a dry field.

It is still a further object of the present invention to provide a self-wetting electrosurgical scalpel and scissors having energized cutting surfaces to which tissue will not adhere due to their wetting.

It is yet a further object of the present invention to provide an electrosurgical cutting and tissue vaporizing instrument which elutes saline.

It is a further object of the present invention to provide a self-wetting electrosurgical cutting and tissue vaporizing instrument which selectively elutes and draws saline at the surgical site.

It is another object of the present invention to provide an electrosurgical cutting and tissue vaporizing instrument which overcomes the inherent disadvantages of known energized and non-energized surgical instruments.

In accordance with one form of the present invention, an electrosurgical tissue transecting and vaporizing instrument employing RF (radio frequency) energy and having the preferred ability to direct saline to the targeted tissue for transection and to remove saline from the targeted tissue by suction is preferably in the form of a scalpel and scissors.

With respect to the electrosurgical scalpel formed in accordance with the present invention, such a scalpel includes a blade portion and a handle portion on which the blade portion is mounted. The handle portion has a generally elongated shape for grasping by a physician, and the blade portion has a generally flat, planar shape. The blade portion defines a sesquipolar electrode tissue cutting and vaporizing member.

The blade portion of the electrosurgical scalpel in accordance with one form of the present invention includes an electrically conductive front section and an electrically conductive rear section, and an electrically non-conductive middle section interposed between and joined to the front and rear sections. The non-conductive middle section separates and electrically insulates the front and rear sections from each other.

The front section of the blade portion has an exposed surface area which is less than the exposed surface area of the rear section of the blade portion so that the front section functions as an active electrode where tissue cutting and vaporization will occur, and the rear section of the blade portion functions as a return electrode. The non-conducting middle section insulates the electrically conductive front section from the electrically conductive rear section, functioning as the active and return electrodes, respectively, so that the two do not short to one another when energized with RF (radio frequency) energy.

One or more ports are formed in either lateral side, or both lateral sides, of either the middle section or the rear section, or both, of the blade portion. These ports communicate with one or more conduits which are formed interiorly of either the middle section or the rear section, or both, of the blade portion and the interior of the handle portion. The conduit or conduits are connectable to either a source of liquid, such as saline, under positive pressure or a source of negative fluid pressure to create suction. In this way, saline may be directed through the conduits and the ports to the targeted tissue area for transection, and if too much saline is present at the targeted tissue area, it may be drawn through the ports by suction.

The electrosurgical scissors formed in accordance with one form of the present invention is similar in many respects to the electrosurgical scalpel previously described. The scissors include a first blade and a second blade which are cross-pivotally joined together. Each of the first and second blades includes an electrically conductive tip portion and a handle portion. Preferably one or both of the handle portions are made of an insulating, electrically non-conductive material, whereas the tip portions of the blades are made from an electrically conductive material. Thus, the non-conductive handle portion or portions of the first and second blades prevent the two tip portions from shorting to one another through the pivotal attachment point of the blades, and the tip portions will not short to one another when they are separated from each other by a predetermined distance.

The exposed surface area of one tip portion is preferably less than the exposed surface area of the other tip portion so that the smaller tip portion of one blade functions as an active electrode where tissue cutting and vaporization will occur, and the larger tip portion of the other blade functions as a return electrode. The electrode tips are energized with preferably bipolar RF (radio frequency) energy.

As with the electrosurgical scalpel of the present invention, the electrosurgical scissors include one or more ports formed on one or more lateral sides of either blade, or both. These ports are in fluid communication with one or more conduits that are formed interiorly of either or both of the blades, which conduits extend along the length of the blade or blades. The conduit or conduits may be connected to a source of pressurized saline and/or to a vacuum source in order to provide saline through the conduit or conduits and one or more ports so that saline will be directed to the targeted area for tissue transection. Also, if too much saline is provided to the targeted area, it may be drawn through the ports and conduits of the scissors by suction.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

An electrosurgical scalpel 2 formed in accordance with one form of the present invention is illustrated by FIGS. 1–4 of the drawings. One of the advantages of the electrosurgical scalpel 2 is that it has the ability to direct saline or another electrolyte to the targeted site for tissue transection and simultaneous vaporization, as well as having the capability of removing saline or other electrolyte from the targeted area if too much of this liquid is provided. This feature advantageously allows the electrosurgical scalpel 2 to be used in dry fields by directing, and removing, saline to and from the targeted area, which further minimizes tissue sticking to the scalpel during transection.

As shown in FIGS. 1–5 of the drawings, an electrosurgical scalpel 2 formed in accordance with one form of the present invention includes a blade portion 4 and a handle portion 6. The blade portion 4 is mounted on the handle portion 6.

Figure 1:
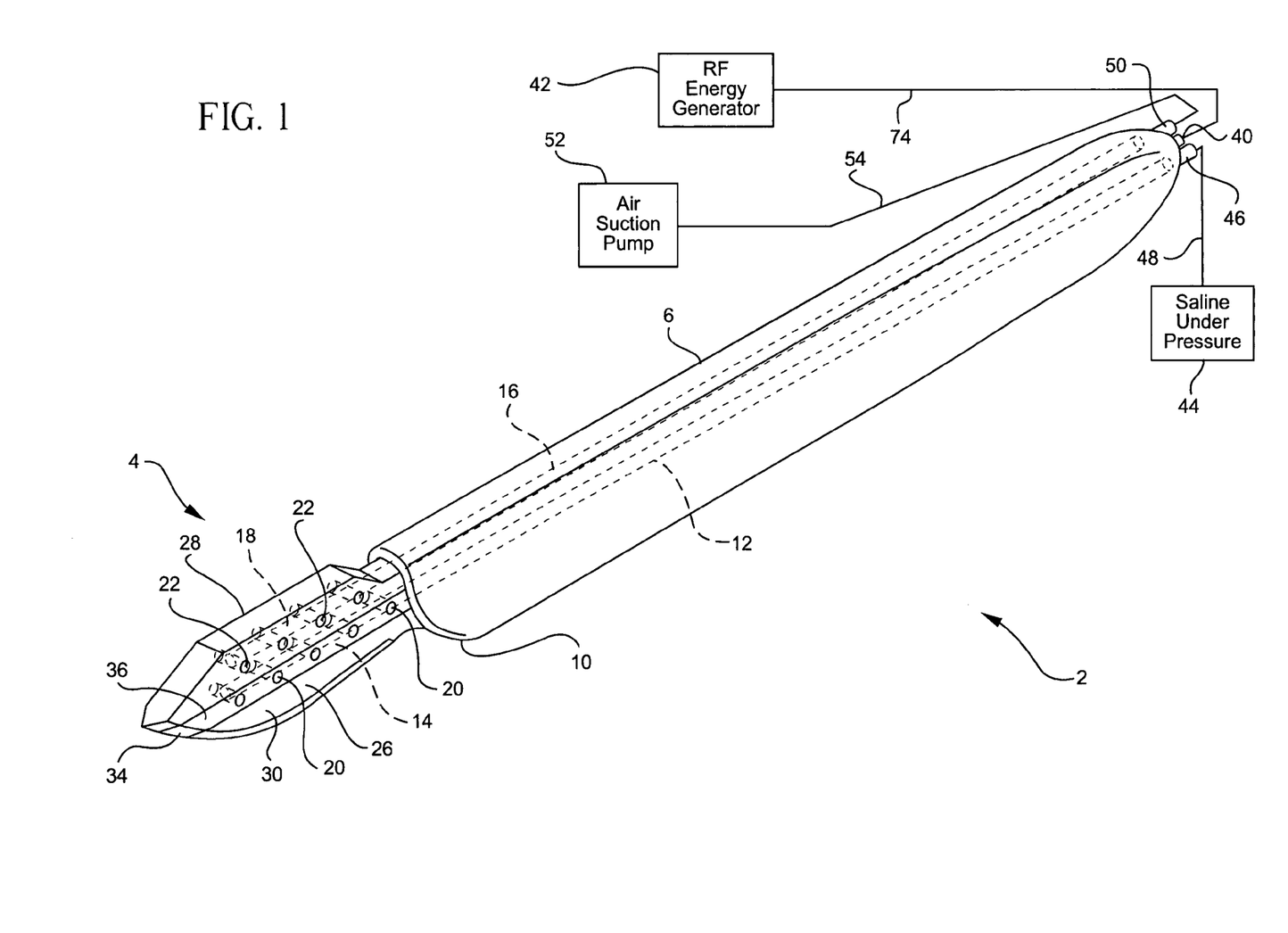
FIG. 1 is a front isometric view of an electrosurgical scalpel formed in accordance with one form of the present invention.
Figure 2:
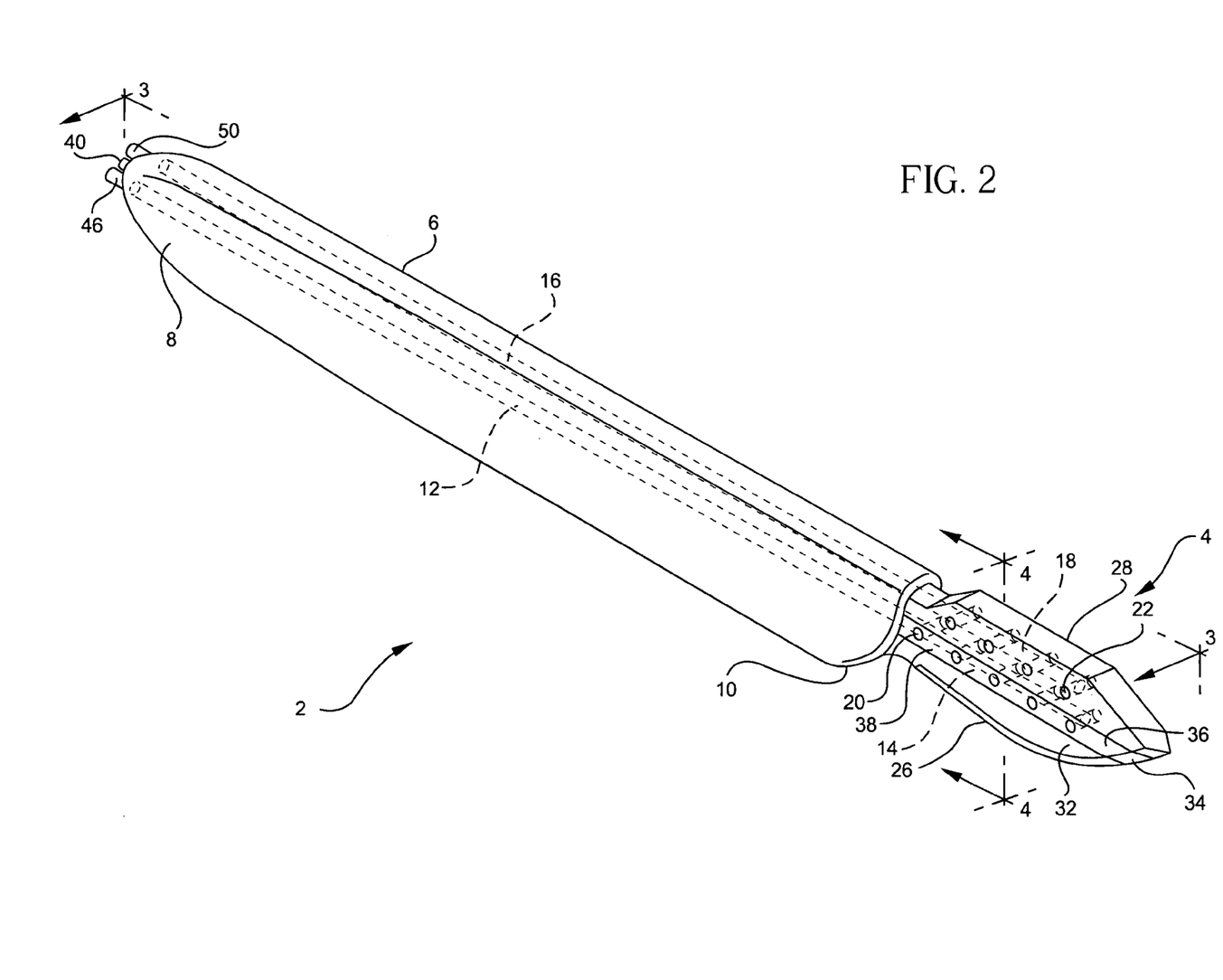
FIG. 2 is a rear isometric view of the electrosurgical scalpel shown in FIG. 1 and formed in accordance with the present invention.

The handle portion 6 has a generally elongated shape, and includes a proximate end 8 for grasping by a physician and a distal end 10 situated opposite the proximate end and on which the blade portion 4 is mounted. The blade portion 4 may be mounted to the distal end 10 of the handle portion 6 by any number of methods well known to those skilled in the art, including chemical bonding, adhesive or mechanical means, such as interlocking and symmetrical T-shaped channels or slots and rails or projections (not shown) formed on one or the other of the blade portion 4 and the handle portion 6. Alternatively, the handle portion 6 may be integrally formed with the blade portion 4. The handle portion 6 may be made of a metallic material, such as stainless steel, or may be made from a thermoplastic or resinous material, such as polypropylene, polyethylene, polycarbonate, polyamide, nylon or the like. The handle portion 6 defines an interior area which may be either solid or hollow through which conduits 12, 14, 16, 18 connected to ports 20, 22 in the blade portion 4, and electrical conductors 24 connected to electrode portions 26, 28 of the blade portion, each of which will be described in greater detail, may pass.

The blade portion 4 has a generally flat, planar shape and defines a sesquipolar electrode tissue cutting and vaporizing member. The blade portion 4 has an electrically conductive front section 26 and an electrically conductive rear section 28. The front and rear sections 26, 28 are generally co-planar with each other, as can be seen from FIG. 4 of the drawings. As can be seen from FIG. 1 and FIG. 2 of the drawings, each of the front section 26 and the rear section 28 of the blade portion 4 includes an exposed first lateral side 30 and an exposed second lateral side 32 situated opposite the first lateral side 30.

The blade portion 4 also has an electrically non-conductive, insulative middle section 34. The insulative middle section 34 has a front side and a rear side situated opposite the front side. The middle section also includes, like the front and rear sections, an exposed first lateral side 36 and an exposed second lateral side 38 situated opposite the first lateral side 36.

The front section 26 of the blade portion 4 is joined to the front side of the insulative middle section 34, and the rear section 28 of the blade portion 4 is joined to the rear side of the insulative middle section 34. Accordingly, the middle section 34 is interposed between the electrically conductive front and rear sections 26, 28 and separates and insulates the front and rear sections so they do not touch and short to each other.

Each of the front section 26 and rear section 28 of the blade portion 4 has an exposed surface area. Preferably, the exposed surface area of the front section 26 of the blade portion is less than the exposed surface area of the rear section 28. The surface area of the front section 26 may be substantially less than the surface area of the rear section 28, for example, such that the exposed surface area of the rear section 28 is equal to or greater than between about three and about ten times the exposed surface area of the front section 26. With its relatively small exposed surface area, the front section 26 of the blade portion 4 functions as an active electrode where tissue cutting and vaporization will occur, and the rear section 28, with its relatively large exposed surface area, functions as a return electrode. Advantageously, no other return electrode or pad is necessary to come in contact with the patient during surgery, as is required with many other electrosurgical instruments.

As mentioned previously, preferably bipolar RF (radio frequency) energy is applied to the front and rear sections of the blade portion through electrical conductors 24 which pass through the handle portion 6 and into the blade portion 4 and which contact the front and rear sections 26, 28 of the blade portion. Such electrical conductors 24 are coupled to a connector 40 mounted on the handle portion 6 so as to allow connection to an RF (radio frequency) energy generator 42 for providing RF power to the front and rear sections 26, 28 of the blade portion.

Also as mentioned previously, one of the advantages of the electrosurgical scalpel 2 of the present invention is that it can direct an electrolyte, preferably saline, or other liquid to the targeted area for tissue transection. Another feature of the electrosurgical scalpel 2 of the present invention is that, if too much saline or electrolyte is provided to the targeted tissue area, it may be removed by suction through the scalpel. The structural features of the electrosurgical scalpel which provide saline to the targeted tissue area and which removes excess saline from the targeted tissue area will now be described.

The blade portion 4 includes one or more ports 20, 22 formed in either or both lateral sides 30, 32, 36, 38 of the middle, front or rear sections 26, 28, 34, or any combination of the three sections. Such ports 20, 22 may be connected to one or more conduits 12, 14, 16, 18 formed or provided in the interior areas of the blade portion 4 and the handle portion 6.

Figure 3:
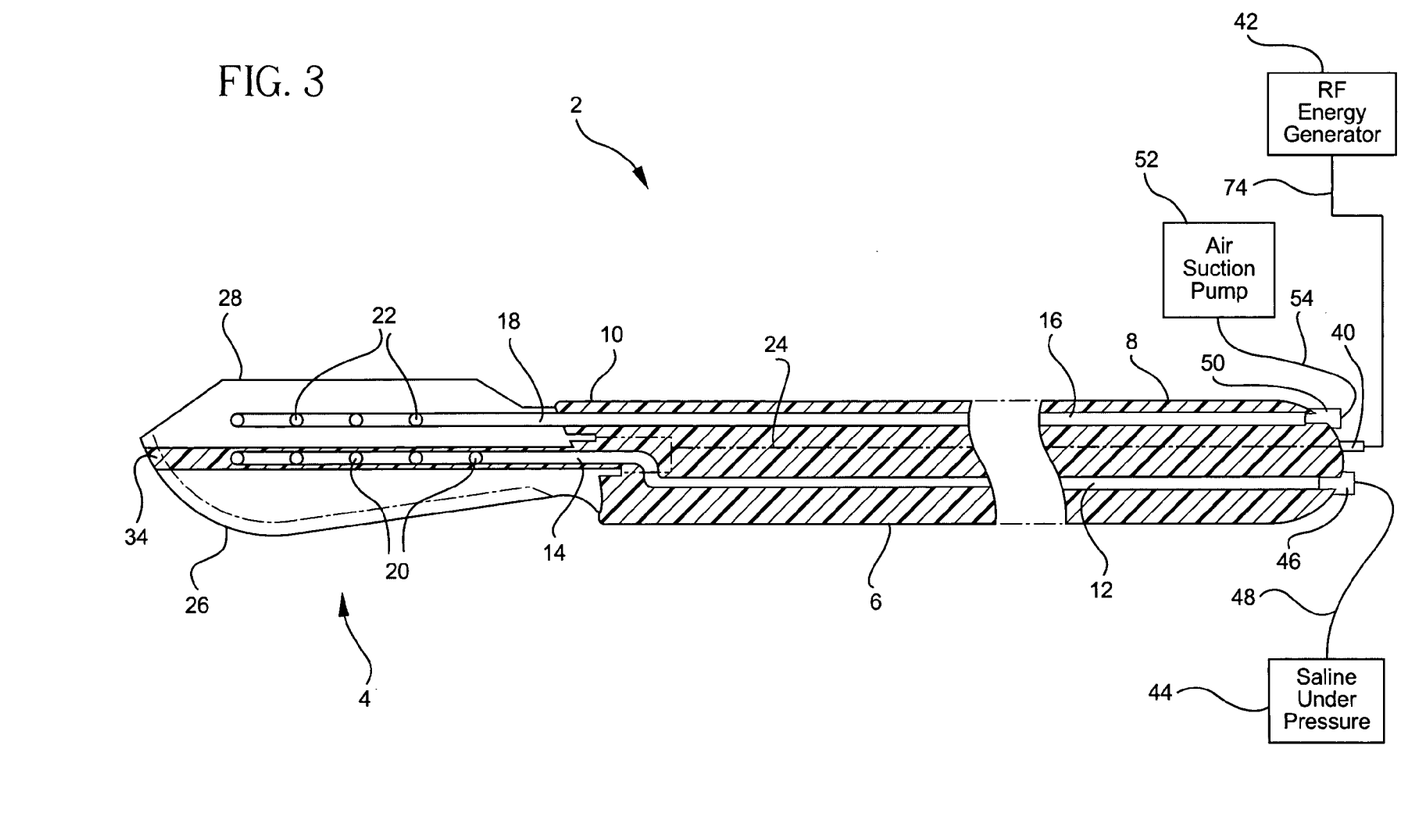
FIG. 3 is a longitudinal cross-sectional view of the electrosurgical scalpel formed in accordance with the present invention and shown in FIG. 2, taken along line 3—3 of FIG. 2.
Figure 4:
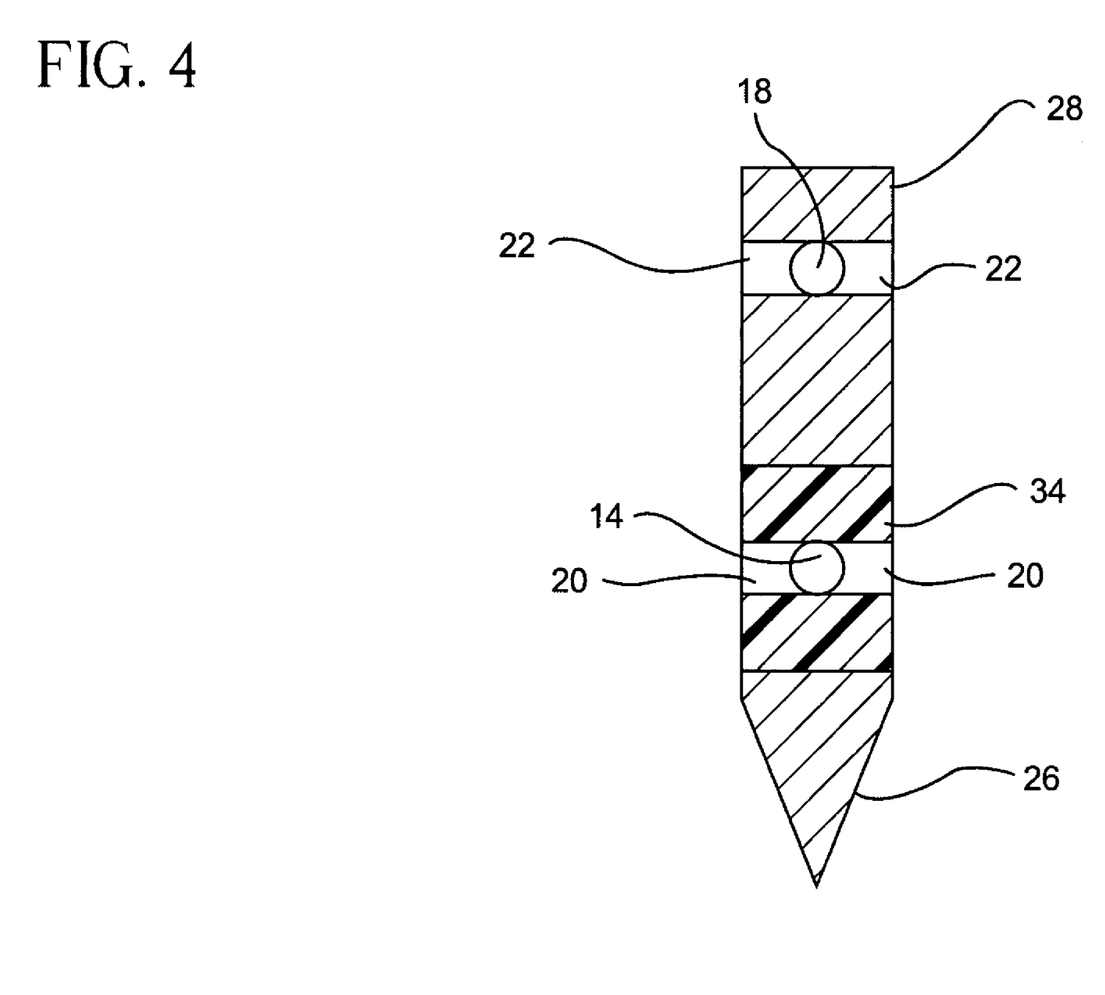
FIG. 4 is a transverse cross-sectional view of the electrosurgical scalpel formed in accordance with the present invention and shown in FIG. 2, taken along line 4—4 of FIG. 2.
Figure 5:
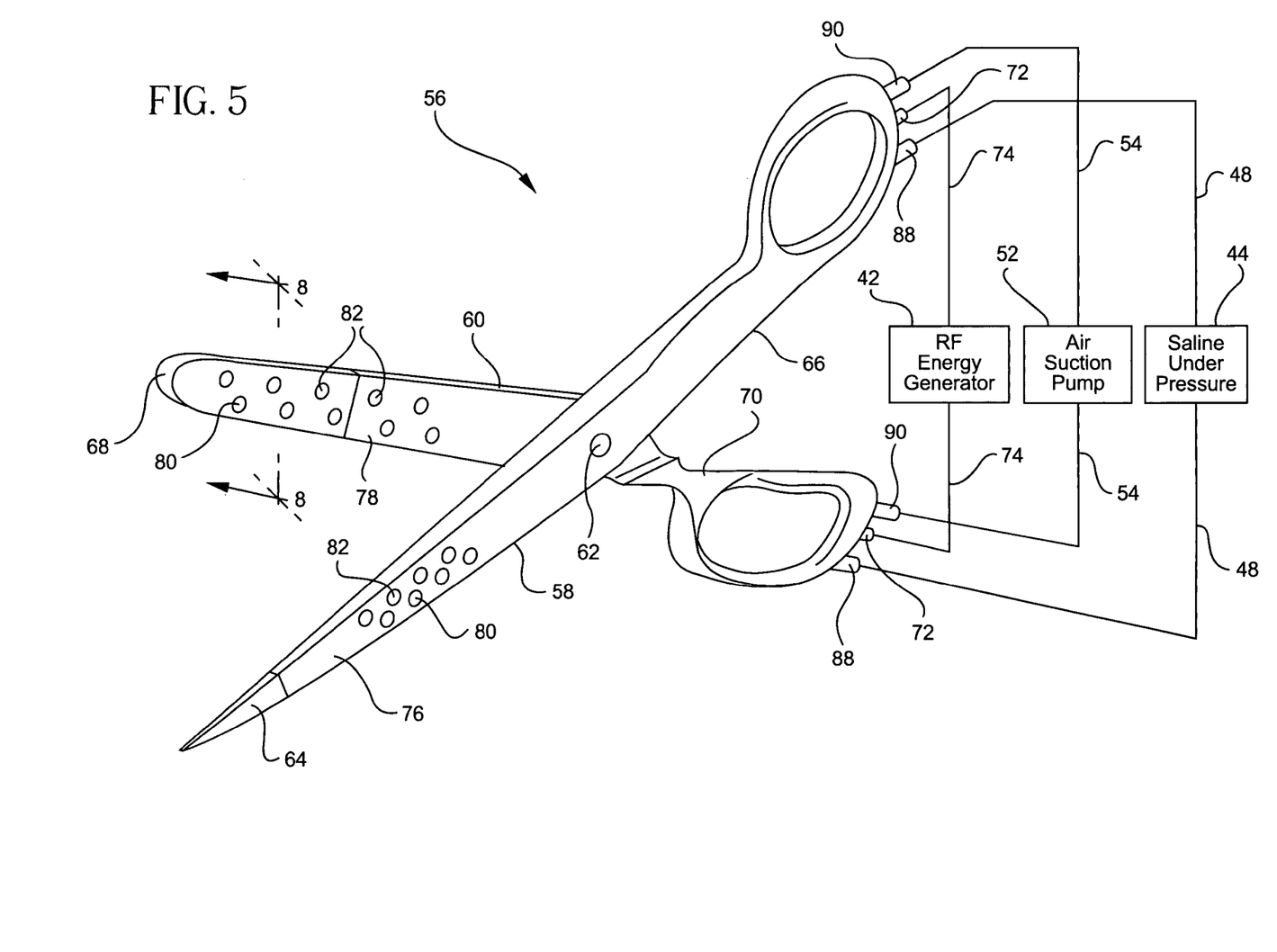
FIG. 5 is a front isometric view of an electrosurgical scissors formed in accordance with one form of the present invention.
Figure 6:
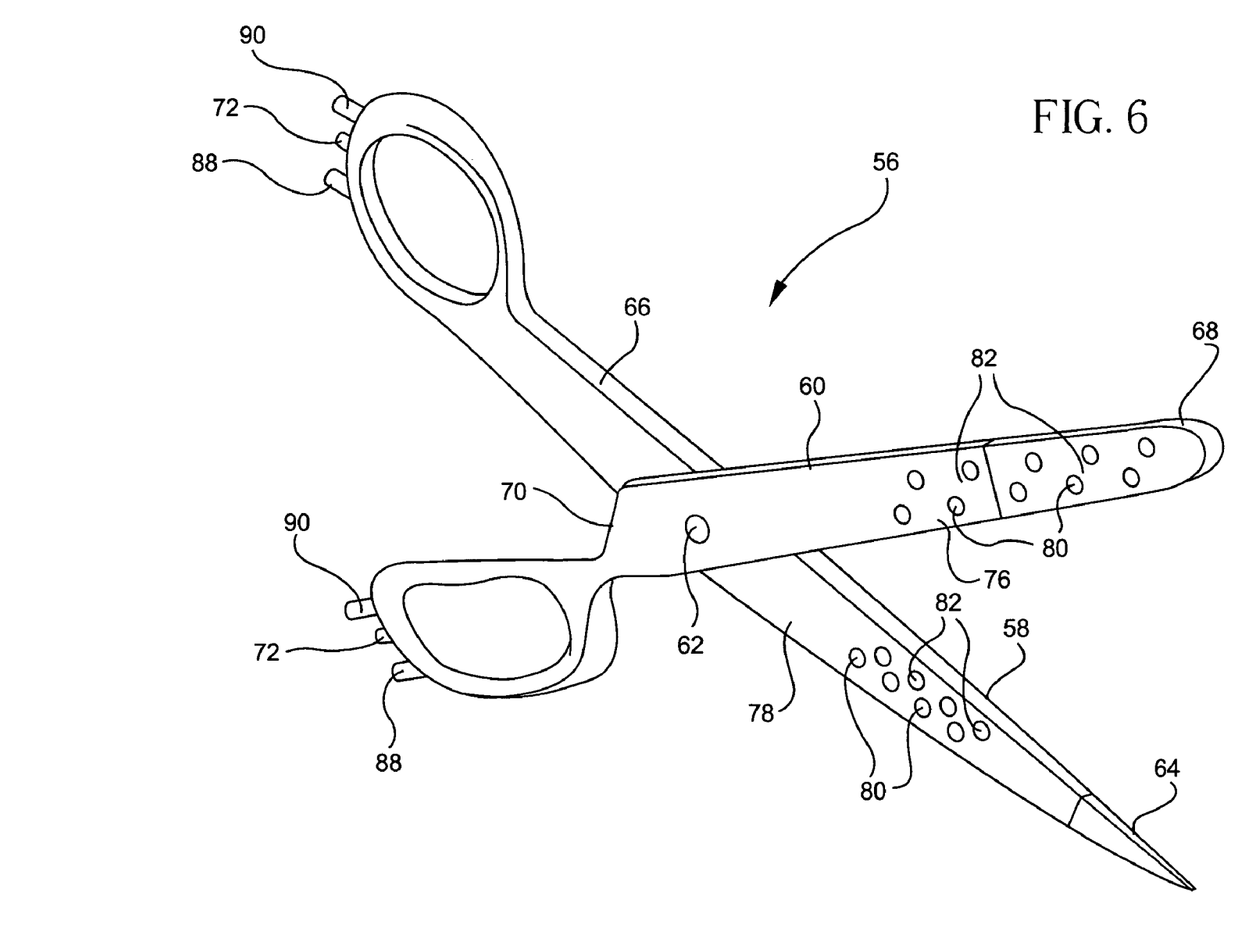
FIG. 6 is a rear isometric view of the electrosurgical scissors shown in FIG. 5 and formed in accordance with the present invention.

More specifically, and as shown in FIG. 3 of the drawings, at least one upper conduit 12 is formed in or passes through the interior of the handle portion 6 at least partially along the longitudinal length thereof and connects with at least one lower conduit 14 which passes through or is formed in the interior area of the blade portion, preferably in either the middle section 34 or the rear section 28 thereof, but which also could be formed in the front section 26. This upper conduit 12 is preferably connected to a source of electrolytic liquid 44, such as saline, under positive pressure through a connector 46 mounted and exposed on the handle portion 6 and external tubing or another conduit 48. The lower conduit 14 may be connected to one or more ports 20 formed in either or both of the middle section 34 and the rear section 28, and/or the front section 26, of the blade portion, which ports 20 may be formed on one lateral side 30 of the blade portion and/or the other lateral side 32. The ports 20 may be connected in series to the conduit 14, as shown in FIG. 3, or in parallel with short conduit taps (not shown) extending from the conduit 14 to each port 20. The ports 20 may also be connected to the conduit 14 alternately, with ports 22 alternately in between connected to a second conduit 18 to which suction is applied, as will be described. The ports 20 are preferably spaced apart from each other in linear columns formed in either or both of the middle and rear sections 34, 28, and/or the front section 26, of the blade portion 4. Thus, preferably saline under pressure is provided from a source 44 to the upper conduit 12, which is in fluid communication with the lower conduit 14 and the port or ports 20 connected thereto. Accordingly, saline is provided preferably on both lateral sides 30, 32 of the blade portion 4 of the scalpel and may be directed to the targeted area for tissue transection when the front and rear electrode sections 26, 28 of the blade portion 4 are energized.

The handle portion 6 preferably also includes another upper conduit 16 formed in or passing through the interior area of the handle portion at least partially along the longitudinal length thereof. This upper conduit 16 is in fluid communication with another lower conduit 18 formed in or passing through the interior area of the blade portion 4. This second lower conduit 16 may pass through one or both of the middle section 34 and the rear section 28, and/or the front section 26, and may be coupled to one or more ports 22 on one or both of the lateral sides 30, 32, 36, 38 of the middle, front or rear sections 34, 26, 28 of the blade portion 4. Like the other lower conduit 14, this second conduit 18 may be coupled to the ports 22 either in series, as shown in FIG. 3, or in parallel, with short conduit taps (not shown) coupled to this second conduit 18 and to individual ports 22. Also, the ports 22 may be connected to this second conduit 18 in an alternating fashion so that alternating ports 20 in between may be connected to the first conduit 14 to elute saline therefrom. Thus, this second upper conduit 16 is in fluid communication with the second lower conduit 18 and to one or more ports 22. The second upper conduit 16 is coupled to a connector 50 mounted and exposed on the handle portion 6 so that an air suction pump 52 may be connected to it by external tubing or another conduit 54 and provides suction through the ports 22, the lower conduit 18 and the upper conduit 16 in order to remove excess saline from the targeted tissue area.

It should be understood that, to facilitate the description of the electrosurgical scalpel 2 formed in accordance with the present invention, only two upper and lower conduits 12, 14, 16, 18 are shown and described. A plurality of air suction and saline conduits may be provided through the handle portion 6 and the blade portion 4 and connected to one or more ports 20, 22. Alternatively, only one conduit may be provided, if desired, through the handle portion 6 and the blade portion 4 and connected to one or more ports 20, 22 formed on either or both lateral sides of the middle and rear sections 34, 28, and/or the front section 26, of the blade portion 4. This one conduit could be alternatingly connected to either an air suction pump 52 or to a source of saline 44 under positive pressure, at the desire of the physician. Also, it should be understood that the communicating upper and lower conduits 12, 14, 16, 18 described herein refer to either separate conduits or upper and lower portions of the same conduit passing through the handle portion 6 and the blade portion 4.

FIGS. 5–8 illustrate an electrosurgical scissors 56 formed in accordance with the present invention. As will be evident from the following description, the electrosurgical scissors 56 have a number of structural features and advantages which are similar in many respects to those of the electrosurgical scalpel 2 described previously. The scissors 56 also have the capability of providing saline to the targeted area for tissue transection, and also the capability of removing excess saline from the targeted area.

As shown in FIGS. 5–8, the electrosurgical scissors 56 of the present invention include a first blade 58 and a second blade 60. The first and second blades 58, 60 are cross-pivotally joined together by a pivot pin 62, screw and nut, rivet or the like.

The first blade 58 includes an electrically conductive tip portion 64 and a handle portion 66, the tip portion 64 being joined to the handle portion 66. The second blade 60, similarly, includes an electrically conductive tip portion 68 and a handle portion 70 to which the tip portion 68 is joined. The tip portion 64, 68 and handle portion 66, 70 of the first and second blades 58, 60 may be joined to each other using a number of methods, such as described previously with respect to the electrosurgical scalpel 2, including chemical bonding, adhesive and mechanical means, such as cooperating and conforming T-shaped channels or slots and rails or projections (not shown) formed on one or the other of the tip portion and the handle portion. Alternatively, the tip portion 64, 68 and handle portion 66, 70 of each blade may be integrally formed together. One or both of the handle portions 66, 70 are formed from an electrically non-conductive and insulative material, such as a thermoplastic material or resin, including polypropylene, polyethylene, polycarbonate, polyamide, nylon or the like. In this way, the tip portion 64 of the first blade 58 will be electrically insulated from the tip portion 68 of the second blade 60 when the two tip portions are separated from each other and are not in contact, that is, when the scissors 56 are open and the tip portions 64, 68 are at least slightly separated from each other by a predetermined distance which, of course, depends on the longitudinal length of each tip portion with respect to the overall length of its respective blade.

Each tip portion 64, 68 of the first and second blades 58, 60 has an exposed surface area. Preferably, the exposed surface area of the tip portion of one blade, for example, the first blade 58, is less than the exposed surface area of the tip portion of the other blade, for example, the second blade 60. Like the electrosurgical scalpel 2 described previously, it is preferred if the exposed surface areas of the two tip portions 64, 68 are substantially different, such as where the exposed surface area of the tip portion 68 of the second blade 60 is equal to or greater than between about three and about ten times the exposed surface area of the tip portion 64 of the first blade 58. In this way, the relatively smaller tip portion 64 of the first blade 58 functions as an active electrode where tissue cutting and vaporization will occur, and where the relatively larger tip portion 68 of the second blade 60 functions as a return electrode.

The tip portions 64, 68 of the first and second blades 58, 60 are connected by electrical conductors (not shown) passing through the interior area of the first and second blades 58, 60 to respective electrical connectors 72 mounted and exposed on the handle portions 66, 70 of the blades. The electrical connectors 72 allow an RF energy generator 42 to be connected through external wires 74 to each connector in order to provide preferably bipolar RF power to the tip portions 64, 68.

Figure 7:
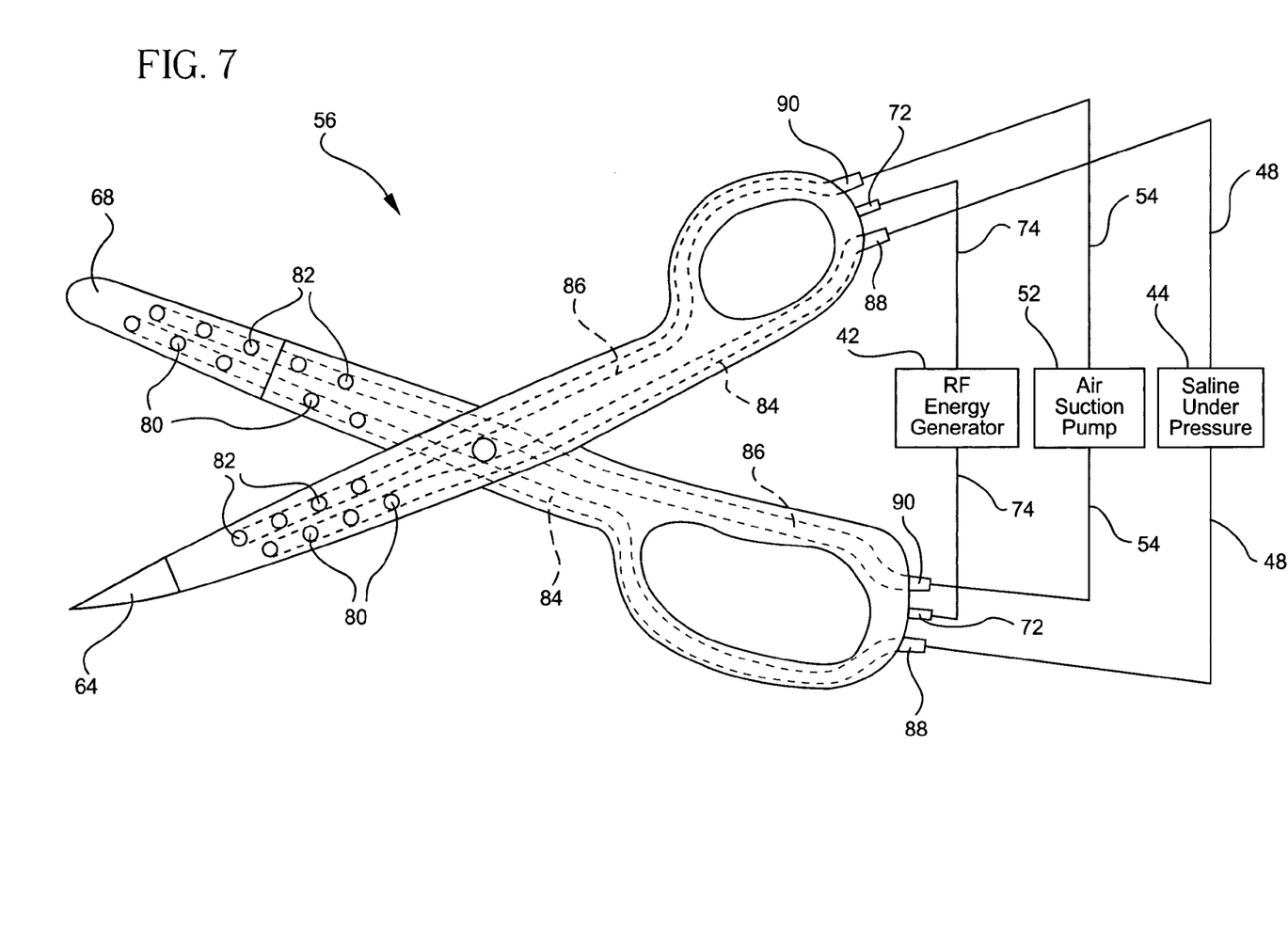
FIG. 7 is a side elevational view of the electrosurgical scissors of the present invention shown in FIG. 5.
Figure 8:
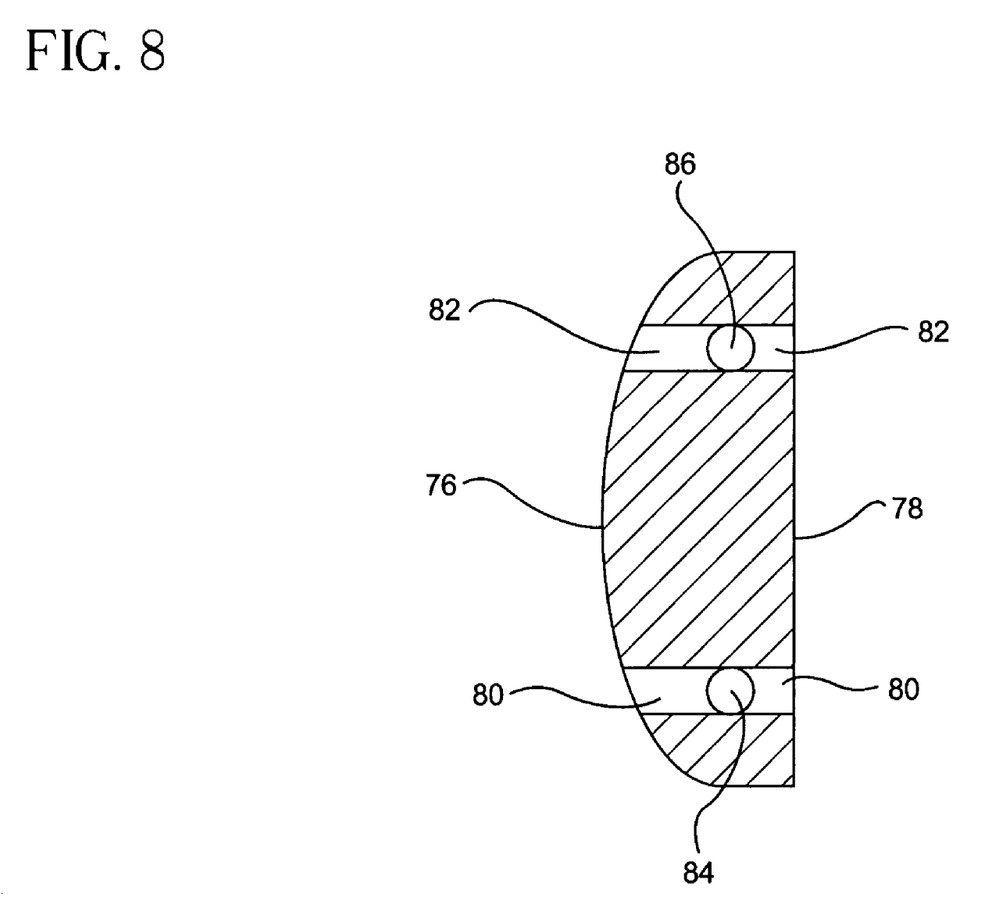
FIG. 8 is a transverse cross-sectional view of the electrosurgical scissors of the present invention shown in FIG. 5, taken along line 8—8 of FIG. 5.

Each of the first and second blades 58, 60 has exposed opposite first and second lateral sides 76, 78, and one or both of the first and second lateral sides 76, 78 has formed therein one or more ports 80, 82. In the interior area of one or both of the first and second blades 58, 60 is formed or passes through at least one conduit 84 which extends along the length of its respective blade and is connected to one or more of the ports 80 formed in the blade. As with the electrosurgical scalpel 2 described previously, the electrosurgical scissors 56 of the present invention preferably have a plurality of ports 80 formed in each blade 58, 60 which are spaced apart from each other and in linear alignment with each other situated along at least a portion of each blade. The conduit 84 formed in one or both of the blades 58, 60 may be connected to the ports 80 in series, as shown in FIG. 7, or in parallel, with short conduit taps (not shown) from the conduit connected to each port. Alternatively, alternate ports 80 may be connected to the conduit 84 and the alternate ports 82 in between may be connected to another conduit 86, as will be described. The conduit 84 is connected to a connector 88 mounted and exposed on the handle portion 66, 70 of the respective blade 58, 60 in which the conduit is formed or passes through, which connector 88 allows a source of saline 44 or other liquid electrolyte to be coupled thereto through an external tube or conduit 48 in order to supply saline or other electrolyte to the conduit. The conduit 84 is in fluid communication with one or more of the ports 80 so that saline under pressure may flow through the conduit and out of the ports to the targeted area for tissue transection.

As shown in FIG. 7, one or both of the first and second blades 58, 60 may include another conduit 86 for providing suction. This second conduit 86 is formed in or passes through the interior area of preferably each blade 58, 60 and is also connected to one or more ports 82 formed in either or both lateral sides 76, 78 of the first blade 58 or the second blade 60, or both. This second conduit 86 is connected to a connector mounted and exposed on the handle portion 66, 70 of the respective blade 58, 60 in which the second conduit 86 is formed so that the blade may be connected to a source of negative fluid pressure 52, such as a vacuum pump or an air suction pump, through an external tube or conduit 54. This second conduit 86 is in fluid communication with one or more ports 82 formed on either or both lateral sides 76, 78 of the first or second blades 58, 60, or both, so that, if too much saline is provided to the targeted tissue area, it may be drawn from the targeted area by suction through the ports 82 and through the second conduit 86 of the scissors.

Of course, it should be understood that, although only two conduits 84, 86 are described and shown in the drawings as being provided in one or both of the first and second blades 58, 60 of the scissors 56, more than two conduits may be provided for eluting saline on the targeted tissue area and for drawing by suction excess saline from the targeted tissue area. Additionally, it should be understood that one or both of the blades 58, 60 may include only one conduit passing therethrough connected to one or more ports 80, 82, where the conduit is selectively or alternately connected to the source of saline 44 or other electrolyte under pressure or the air suction pump 52 to either elute saline on the targeted tissue area or to draw excess saline from the targeted tissue area.

The electrosurgical instruments of the present invention described herein have the advantage over known electrosurgical instruments, especially scalpels and scissors, by providing saline to the targeted area for tissue transection and removing excess saline from the targeted area. Thus, the electrosurgical instruments of the present invention may be used in dry fields. The scalpel 2 and scissors 56 of the present invention provide localized RF (radio frequency) current flow between the active and return electrodes due to the saline wetting of the targeted tissue area. The electrosurgical instruments not only have the ability to transect tissue, but also simultaneously provides hemostasis during tissue transection. Additionally, because of the ports situated in proximity to the cutting area of the scalpel 2 and scissors 56, the electrosurgical instruments of the present invention minimize the adherence of tissue to the electrodes and, in particular, the cutting surfaces due to the saline or other electrolyte liquid provided through the ports. Furthermore, each of the scalpel 2 and scissors 56 has its own return electrode, and so no return pad need be adhered to the patient. The electrosurgical instruments of the present invention not only transect tissue but also vaporize the transected tissue to minimize bleeding. The vaporization has a shallow depth of heat penetration to limit any lateral damage during use of the electrosurgical instruments.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An electrosurgical scalpel, which comprises:
a blade portion and a handle portion, the blade portion being mounted on the handle portion, the handle portion having a generally elongated shape and a proximate end for grasping by a physician and a distal end situated opposite the proximate end and on which the blade portion is mounted, the blade portion having a generally flat, planar shape and defining a sesquipolar electrode tissue cutting and vaporizing member, the blade portion having an electrically conductive front section and an electrically conductive rear section, the front and rear sections being generally co-planar with each other, and further having an electrically insulative middle section, the insulative middle section having a front side and a rear side situated opposite the front side, at least one of the middle section, the rear section and the front section having an exposed first lateral side and an exposed second lateral side situated opposite the first lateral side, the front section of the blade portion being joined to the front side of the insulative middle section, and the rear section of the blade portion being joined to the rear side of the insulative middle section, each of the front section and the rear section of the blade portion having an exposed surface area, the exposed surface area of the front section of the blade portion being less than the exposed surface area of the rear section of the blade portion, whereby the front section of the blade portion functions as an active electrode where tissue cutting and vaporization will occur, and whereby the rear section of the blade portion functions as a return electrode, the at least one of the insulating middle section, the rear section and the front section having an interior area and at least one lower conduit formed in the interior area thereof, and further having at least one port formed in at least one of the first and second lateral sides thereof, the at least one port being in fluid communication with the at least one lower conduit, the handle portion having an interior area and at least one upper conduit formed in the interior area thereof, the at least one upper conduit of the handle portion being in fluid communication with the at least one lower conduit of the at least one of the middle section, the rear section and the front section of the blade portion to allow the passage of a liquid under at least one of a positive pressure and a negative pressure to pass through the at least one upper conduit, the at least one lower conduit and the at least one port.

2. An electrosurgical scalpel as defined by claim 1, wherein at least one first port is formed in the first lateral side of the at least one of the middle section, the rear section and the front section of the blade portion; wherein at least one second port is formed in the second lateral side of the at least one of the middle section, the rear section and the front section of the blade portion; and wherein the at least first and second ports are in fluid communication with the at least one lower conduit and the at least one upper conduit.

3. An electrosurgical scalpel as defined by claim 2, wherein at least one first lower conduit is formed in the interior area of the at least one of the middle section, the rear section and the front section, at least one second lower conduit is formed in the interior area of the at least one of the middle section, the rear section and the front section, at least one first upper conduit is formed in the interior area of the handle portion, and at least one second upper conduit is formed in the interior area of the handle portion, the at least one first upper conduit being in fluid communication with the at least one first lower conduit, and the at least one first port being in fluid communication with the at least one first lower conduit and the at least one first upper conduit, the at least one second upper conduit being in fluid communication with the at least one second lower conduit, and the at least one second port being in fluid communication with the at least one second lower conduit and the at least one second upper conduit.

4. An electrosurgical scalpel as defined by claim 3, wherein the at least one first upper conduit of the handle portion is operatively connectable to a source of liquid under positive pressure to cause the liquid to flow through the at least one first upper conduit, the at least one first lower conduit and the at least one first port.

5. An electrosurgical scalpel as defined by claim 4, wherein the liquid is saline.

6. An electrosurgical scalpel as defined by claim 3, wherein the at least one second upper conduit of the handle portion is operatively connectable to a source of negative fluid pressure to cause the liquid to flow through the at least one second upper conduit, the at least one second lower conduit and the at least one second port.

7. An electrosurgical scalpel as defined by claim 6, wherein the source of negative fluid pressure is an air suction pump.

8. An electrosurgical scalpel as defined by claim 3, wherein the at least one first upper conduit of the handle portion is operatively connectable to a source of liquid under positive pressure to cause the liquid to flow through the at least one first upper conduit, the at least one first lower conduit and the at least one first port; and wherein the at least one second upper conduit of the handle portion is operatively connectable to a source of negative fluid pressure to cause the liquid to flow through the at least one second upper conduit, the at least one second lower conduit and the at least one second port.

9. An electrosurgical scalpel as defined by claim 8, wherein the liquid is saline and the source of negative fluid pressure is an air suction pump.

10. An electrosurgical scalpel as defined by claim 2, wherein the first lateral side of the at least one of the middle section, the rear section and the front section of the blade portion has formed therein a plurality of spaced apart first ports in fluid communication with the at least one lower conduit and the at least one upper conduit.

11. An electrosurgical scalpel as defined by claim 3, wherein the first lateral side of the at least one of the middle section, the rear section and the front section of the blade portion has formed therein a plurality of spaced apart first ports in fluid communication with the at least one first lower conduit and the at least one first upper conduit; and wherein the second lateral side of the at least one of the middle section, the rear section and the front section of the blade portion has formed therein a plurality of spaced apart second ports in fluid communication with the at least one second lower conduit and the at least one second upper conduit.

12. An electrosurgical scalpel as defined by claim 1, wherein the exposed surface area of the rear section of the blade portion is equal to between about three and about ten times the exposed surface area of the front section of the blade portion.

* * * * *